Sept. 16, 1975 J. C. MIKKELSEN Plant Pat. 3,784
BEGONIA PLANT
Filed March 7, 1974
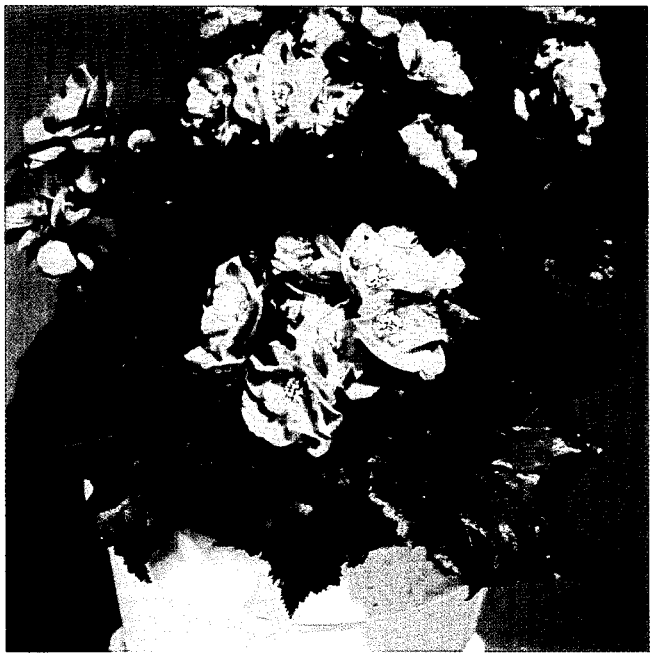

United States Patent Office

Plant Pat. 3,784
Patented Sept. 16, 1975

3,784
BEGONIA PLANT

James C. Mikkelsen, Ashtabula, Ohio, assignor to Mikkelsens Inc., Ashtabula, Ohio Filed Mar. 7, 1974, Ser. No. 449,019
Int. Cl. A01h 5/00
U.S. Cl. Plt.—68 1 Claim The present invention relates to a new and distinctive cultivar of begonia plant, known by the varietal name Ruffled Schwabia and botanically known as *Begonia elatior*. The new cultivar was discovered by me as a bud mutation appearing on one side of a flowering plant of Riegers Schwabenland, the parent cultivar being disclosed in U.S. Plant Pat. 3,320, granted Mar. 13, 1973, to Otto Rieger, deceased. Asexual reproduction by stem and leaf cuttings has reproduced the unique features of the new cultivar through successive propagations.

The following characteristics distinguish the new begonia from both its parent and other begonias commercially known and used in the floriculture industry:

1. Much deeper red and brighter color of the tepals compared to parent cultivar.
2. Under optimum conditions of flower initiation (65° F. with 12 hour day) there is consistent tendency to have 5 and 6 tepals per flower compared to 4 in most cultivars of this type.
3. Slower growing than parent cultivar.
4. Darker green foliage than parent cultivar.
5. Heavier foliage with more indentations on edges.
6. Slower rooting than parent cultivar.
7. Greater number of flowers maintained in bloom at any one time than parent cultivar.
8. Flower texture and quality is superior to parent cultivar.

The accompanying colored photographic drawing illustrates the overall appearance of the new cultivar taken as a face view of the plant. It is noted that the tepal color in the drawing closely represents the actual color value but the foliage color is darker than the actual foliage color. However, the correct color values for the foliage appear in the following description.

The following is a detailed description of the new begonia based on plants produced under commercial practices in the greenhouses of Mikkelsens Inc., Ashtabula, Ohio. Color references are made to the Royal Horticultural Society Colour Chart except where general color terms of ordinary dictionary significance are used.

*Parentage*: Mutation from Riegers Schwabenland.

*Propagation*: Basically by leaf cuttings rooting somewhat slower than the parent variety producing adventitious buds at the base of the leaf petiole. Rooting is in about 4–5 weeks and development of adventitious shoots is an additional 7–8 weeks, thereby resulting in total production time of 11–13 weeks.

*Rooting Habit*: Profuse, fibrous, fine textured roots.

*Form*: Plant is round/bushy.

*Habit of Growth*: Upright, vigorous, self-supporting. When fully grown, the new cultivar is approximately 8″–10″ in height and 8″–10″ in diameter.

*Blooming Habits*: Flowering can be controlled. When flowering has been initiated blooms will continue to appear for many months.

*Blooming Season*: Natural flowering season is late November to early December in the latitude of Ohio.

*Foliage*: Plentiful, lush, dark green, having strong petioles attached to the stem at a close angle. Alternate.

- *Size*—Average being 8–12 cm. long; 5–8 cm. wide.
- *Shape*—Cordate, crenate, quite wavy at edges of each lobe.
- *Texture*—Heavy, crisp, glabrous.
- *Margin*—Heavily serrated when young, less defined in mature foliage.
- *Color*—Old: top—135A–B; under—138B.

*Disease Resistance*: Appears to be more resistant to common powdery mildew than the parent variety fhich in turn is quite resistant compared to older cultivars of this type of begonia.

*Flowers*:

- *Borne*—Tends toward more compact clustering of flowers in the cyme. Flower pedicels and cyme peduncle are quite rigid and thick giving excellent support for each flower. Individual blooms last approximately 2–4 weeks.
  - *Quantity*—The total abundance of flowers is comparable to parent variety.
- *Buds*—Flat, folded, round, opening to a semi-cupped flower with first two tepals flat and remaining tepals cupped or reflexed inward toward the stamens.
- *Tepals*—Are 5–6 in number, compared to the usual 4; edges are ruffled, inner tepals are refluxed; color, top red 42A; under, red 44C, compared to 44A–B top color and 42A bottom color of parent cultivar Schwabenland.
- *Reproduction Organs*: Stamens—Abundant, anthers larger than on parent variety, color yellow 13–3. Pollen—Yellow 13D. Styles/ovaries—None observed to date.

I claim:

1. A new and distinctive cultivar of *elatior* begonia characterized particularly by its bright, deep red flower color; consistent tendency to have 5–6 tepals per flower; relatively slow rooting and growth habits; dark green, heavy foliage with indentations on edges; superior flower texture and quality, and by its ability to maintain greater numbers of flowers in bloom at any one time when compared to the parent cultivar Schwabenland.

No references cited.

ROBERT E. BAGWILL, Primary Examiner